United States Patent
Kojima et al.

(10) Patent No.: US 9,508,142 B2
(45) Date of Patent: Nov. 29, 2016

(54) X-RAY CT APPARATUS AND X-RAY CT IMAGE-GENERATING METHOD

(71) Applicants: Hitachi Medical Corporation, Chiyoda-ku, Tokyo (JP); Yukiko Ueki, Chiyoda-ku, Tokyo (JP)

(72) Inventors: Shinichi Kojima, Tokyo (JP); Keisuke Yamakawa, Tokyo (JP); Hisashi Takahashi, Tokyo (JP); Hironori Ueki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 121 days.

(21) Appl. No.: 14/422,788

(22) PCT Filed: Aug. 7, 2013

(86) PCT No.: PCT/JP2013/071404
§ 371 (c)(1),
(2) Date: Feb. 20, 2015

(87) PCT Pub. No.: WO2014/030543
PCT Pub. Date: Feb. 27, 2014

(65) Prior Publication Data
US 2015/0221085 A1    Aug. 6, 2015

(30) Foreign Application Priority Data
Aug. 22, 2012   (JP) ................. 2012-183333

(51) Int. Cl.
*G06K 9/00* (2006.01)
*G06T 7/00* (2006.01)
(Continued)

(52) U.S. Cl.
CPC .......... *G06T 7/0012* (2013.01); *A61B 6/4233* (2013.01); *A61B 6/5258* (2013.01);
(Continued)

(58) Field of Classification Search
CPC ............... G06T 7/0012; G06T 7/0081; G06T 2207/10081; G06T 11/003; G01N 23/046; A61B 6/0306
See application file for complete search history.

(56) References Cited

U.S. PATENT DOCUMENTS 4,392,237 A * 7/1983 Houston ................ G01N 23/10
250/358.1
4,910,786 A * 3/1990 Eichel .................... G06T 7/0083
382/199

(Continued)

FOREIGN PATENT DOCUMENTS

JP    2005-204858 A    8/2005
JP    2005-319152 A    11/2005

(Continued)

OTHER PUBLICATIONS

International Search Report (PCT/ISA/210) dated Nov. 12, 2013, with English translation (two 2) pages).
(Continued)

*Primary Examiner* — Amir Alavi
(74) *Attorney, Agent, or Firm* — Crowell & Moring LLP

(57) ABSTRACT

An X-ray detector (320), configured to have X-ray detecting elements (322) arranged in array, detects the intensity of X-rays that are radiated from the X-ray tube (311) and have passed through a subject (500). A data processing device (420) executes steps of: arranging scan data, which is based on the intensity of X-rays, in an array sequence of the X-ray detecting elements (322) or in a time sequence, to detect an anomalous scan data; associating a weight greater than "1" with scan data adjacent to the anomalous scan data, and associating a weight of "1" with other imaging data; calculating an update amount of a pixel vector that reflects these weights; and performing an iterative operation using the update amount to generate an X-ray CT image of the subject (500).

14 Claims, 9 Drawing Sheets

(51) Int. Cl.
*A61B 6/00* (2006.01)
*G01N 23/04* (2006.01)
*G06T 5/00* (2006.01)
*A61B 6/03* (2006.01)

(52) U.S. Cl.
CPC .......... *G01N23/046* (2013.01); *G06T 5/005* (2013.01); *A61B 6/03* (2013.01); *G06T 2207/10081* (2013.01); *G06T 2207/30004* (2013.01)

(56) References Cited

U.S. PATENT DOCUMENTS

| | | | | |
|---|---|---|---|---|
| 5,181,234 A * | 1/1993 | Smith | ................ | G01V 5/0025 250/472.1 |
| 5,974,108 A * | 10/1999 | Taguchi | ................ | G06T 11/005 378/15 |
| 6,410,921 B1 * | 6/2002 | Nakazawa | ............ | G01T 1/2928 250/208.1 |
| 6,430,253 B1 * | 8/2002 | Oikawa | ................ | A61B 6/027 378/15 |
| 6,873,679 B2 * | 3/2005 | Hagiwara | ............ | G06T 11/005 378/15 |
| 7,813,470 B2 * | 10/2010 | Kuwabara | ........... | G01N 23/087 378/4 |
| 7,970,096 B2 * | 6/2011 | Pavlovich | ............. | A61B 6/032 378/156 |
| 8,175,217 B2 * | 5/2012 | Sugaya | ................. | A61B 6/032 378/16 |
| 2010/0046818 A1 | 2/2010 | Yamaya et al. | | |
| 2015/0221085 A1 * | 8/2015 | Kojima | ................ | A61B 6/4233 382/131 |

FOREIGN PATENT DOCUMENTS

JP 2008-245695 A 10/2008
JP 2013-85735 A 5/2013

OTHER PUBLICATIONS

Japanese-language Written Opinion (PCT/ISA/237) dated Nov. 12, 2013 (four (4) pages).

* cited by examiner

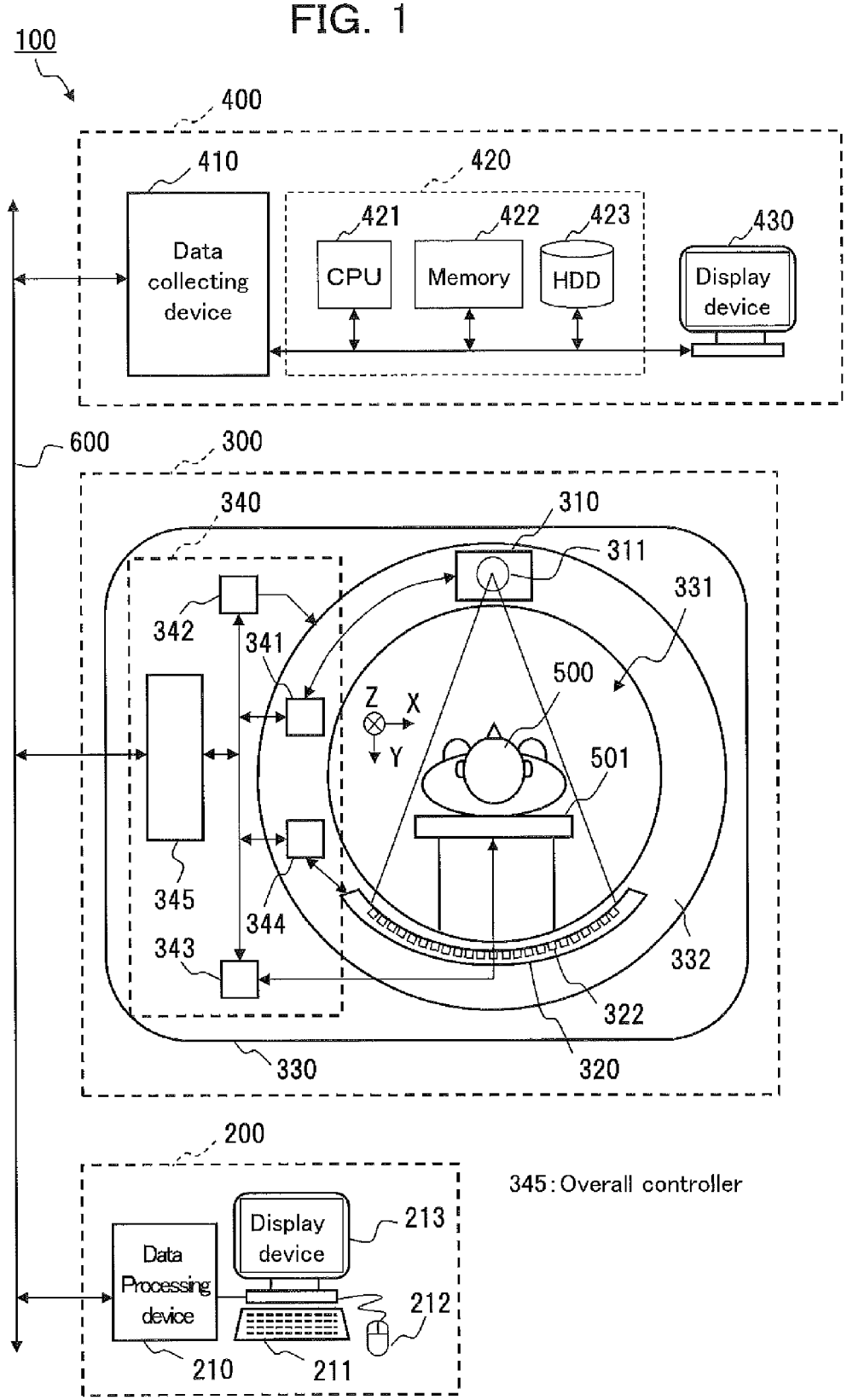

X-RAY CT APPARATUS AND X-RAY CT IMAGE-GENERATING METHOD

This application is a 371 of PCT/JP2013/071404 Aug. 7, 2013

TECHNICAL FIELD

The present invention relates to an X-ray CT (Computed Tomography) apparatus and an X-ray CT image-generating method.

BACKGROUND ART

An X-ray CT apparatus is an apparatus which includes an X-ray source that x-irradiates a subject and an X-ray detector that is arranged at a position facing to the X-ray source to detect X-rays passing through the subject. Then, the X-ray source and X-ray detector is rotated around the subject to scan transmission images of the subject from multiple directions. A computer included in the X-ray CT apparatus processes the transmission images of the subject scanned from the multiple directions to generate a structure inside the subject as a tomographic image or a three-dimensional image, based on an X-ray absorption rate inside of the subject.

As the X-ray CT apparatus is for medical use, if an artifact is caused in an X-ray CT image, suitable diagnosis of a disease or its indication is disrupted. Also, when the diagnosis fails, the exposure given to the subject turns to be an unnecessary exposure. Therefore, the incidence of failures, such as an output signal of the X-ray detector becoming anomalous, needs to be reduced as much as possible to allow the X-ray CT apparatus to stably operate, and to prevent an artifact from being caused.

Japanese Patent Application Publication No. 2008-245695 discloses a technique with which, when the position of an X-ray detecting element which has failed (hereinafter referred to as a fault X-ray detecting element) is identified in an X-ray detector composed of a number of X-ray detecting elements, an X-ray CT image is generated in iteration, without using detection data obtained from the fault X-ray detecting element, to improve quality of the image.

SUMMARY OF THE INVENTION

Problems to be Solved

In the technique disclosed in Japanese Patent Application Publication No. 2008-245695, anomalous detection data obtained from the fault X-ray detecting device is not allowed for use in iterative processing to generate an X-ray CT image. In that case, iterative processing is not performed for a direction connecting the fault X-ray detecting element and the X-ray source. This means that the iterative processing is not performed for converging the image, which is in the direction in which the artifact is caused, into a correct image. In this case, as the image in the direction in which the artifact is caused is corrected by iterative processing using detection data obtained from those other than the fault X-ray detecting element, there is a demerit that convergence of the iterative processing takes longer.

Then, the present invention is intended to provide an X-ray CT apparatus and an X-ray generating method, each of which can obtain an X-ray CT image, in which even if anomalous data is detected from an X-ray detecting element, an artifact is not caused by the anomalous data, by rapidly converging the image through an iterative operation.

Solution to Problems

An X-ray CT apparatus according to the present invention includes: an X-ray generator that generates X-rays; an X-ray detector that is configured to have multiple X-ray detecting elements arranged in array for detecting intensity of the X-rays; a scanning control unit that transmits detection data detected by the X-ray detecting elements as scan data of a subject; and a data processing device that obtains the scan data transmitted from the scanning control unit, and processes the obtained scan data to generate an X-ray CT image of the subject.

Then, the data processing device is characterized to execute: a step of storing the scan data obtained by the X-ray detecting elements into a storage unit in accordance with the arrangement of the X-ray detecting elements in the X-ray detector, and detecting anomalous scan data among the stored scan data; a step of associating a weight with scan data adjacent to the anomalous scan data detected, the weight being greater than a weight associated with other scan data; and a step of, through iteration of an iterative operation using a projection matrix defined by data including a layout position of the X-ray generator and arrangement positions of the respective multiple X-ray detection elements, pixel data that has been set at that time, and the scan data, calculating the pixel data of the X-ray CT image of the subject, wherein in the iterative operation, when calculating an update amount for the pixel data based on difference data between projection data obtained from the projection matrix and the pixel data at that time, and the scan data, the difference data is weighted with the weight associated with the scan data corresponding to the difference data.

Advantageous Effects of the Invention

According to the present invention, with an X-ray CT apparatus and an X-ray CT image-generating method, even if anomalous data is detected from an X-ray detecting element, an X-ray CT image can be obtained that has no artifact caused by the anomalous data, by rapidly converging the image through an iterative operation.

BRIEF DESCRIPTION OF DRAWINGS

FIG. 1 is a diagram schematically showing an exemplary configuration of an X-ray CT apparatus according to a first embodiment of the present invention.

FIG. 2A is a cross-sectional view taken along a plane parallel to the x-y plane, and FIG. 2B is a top view of the X-ray detector arranged on the x-z plane as seen from the top in the y direction.

EMBODIMENTS OF THE INVENTION

Figure 2A:
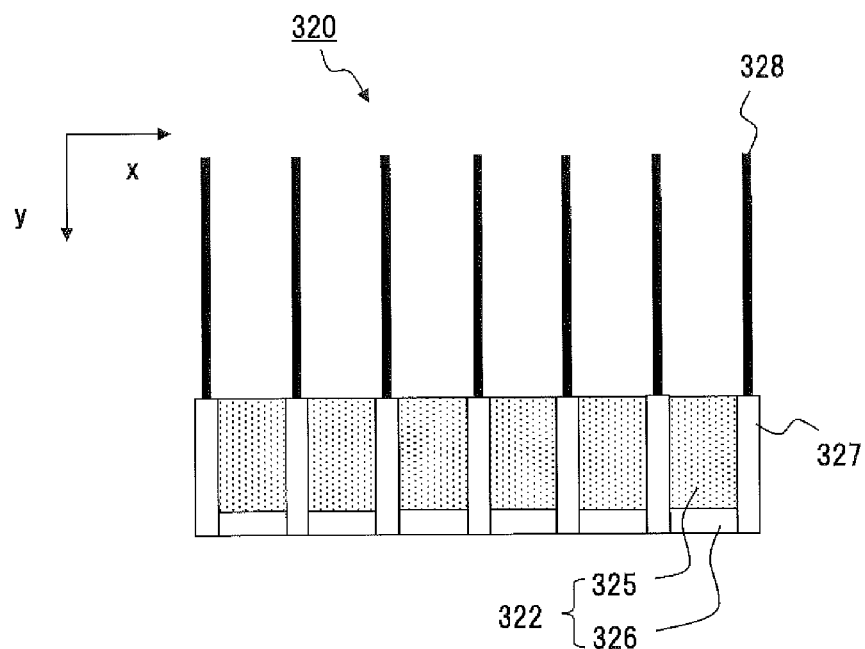
FIGS. 2A and 2B are schematic views showing enlarged portions of the X-ray detector, where

Hereinafter, embodiments of the present invention will be described in detail with reference to the drawings.

First Embodiment

At first, in the first embodiment, a description will be given of an exemplary configuration of an X-ray CT apparatus that rapidly corrects an artifact caused by a failure of an X-ray detecting element, and an example of generating an X-ray CT image.

FIG. 1 is a diagram schematically showing an exemplary configuration of an X-ray CT apparatus according to a first embodiment of the present invention.

As shown in FIG. 1, an X-ray CT apparatus 100 according to the present embodiment is configured to include an X-ray apparatus 300, an image generator 400, and an operation terminal 200 that are interconnected via a communication line 600. Hereinafter, a description will be given of a detailed configuration of each of the X-ray apparatus 300, the image generator 400 and the operation terminal 200.

<Configuration of X-Ray Apparatus 300>

The X-ray apparatus 300 includes: an X-ray generator 310 composed of an X-ray tube 311 that generates X-rays; an X-ray detector 320 composed of multiple X-ray detecting elements 322; a gantry 330; a scanning control unit 340; a subject table 501 on which a subject 500 is placed; and the like.

The gantry 330 is a housing that has a bore 331 in a circular shape which is perpendicular to a horizontal floor, and rotatably supports a rotating body 332 in an annular shape which is fitted into the bore 331. The subject table 501 placed with the subject 500 is arranged so as to be inserted into a ring portion (the bore 331 of the gantry 330) of the rotating body 332 in an annular shape.

In addition, the interior of the gantry 330 houses inside thereof: a drive mechanism, not shown, for rotating the rotating body 332; scanning control unit 340; and the like. Also, the subject table 501 is provided with a drive mechanism, not shown, for adjusting the position of the subject 500 to the rotating body 332.

Further, in the rotating body 332, the X-ray generator 310 is arranged so as to radiate generated X-rays toward the rotation axis of the rotating body 332, and also the X-ray detector 320 is arranged at a position opposed to the position, where the X-ray generator 310 is arranged, centering around the rotation axis of the rotating body 332. In this case, the X-ray generator 310 and the X-ray detector 320 are fixed to the rotating body 332 to rotate with the rotation of the rotating body 332.

The scanning control unit 340 is configured to include: an X-ray generation controller 341 that controls generation of X-rays in the X-ray generator 310; a gantry controller 342 that controls rotation drive of the rotating body 332; a table controller 343 that controls the position to which the subject table 501 is moved; an X-ray detector controller 344 that controls an operation of the X-ray detector 320 at the time of imaging; and an overall controller 345 that controls all the operations of these controllers 341 to 344.

In FIG. 1, X-rays radiated from the X-ray tube 311 pass through the subject 500 to reach the X-ray detector 320, where the intensity of the X-rays is detected by the respective X-ray detecting elements 322 of the X-ray detector 320. In this embodiment, the distance from the point of the X-ray tube 311 where the X-rays are generated to the surface of the X-ray detector 320 where the X-rays are received may be set to 1,000 mm and the diameter of the bore 331 of the rotating body 332 framed in the gantry 330 may be set to 700 mm.

In addition, in FIG. 1, the plane of rotation of the rotating body 332 may be perpendicular to a horizontal floor, the directions of horizontal lines and vertical lines included in the plane of rotation may be defined as an x-direction and a y-direction, respectively, and the direction perpendicular to the plane of rotation may be defined as a z-direction.

Figure 2B:
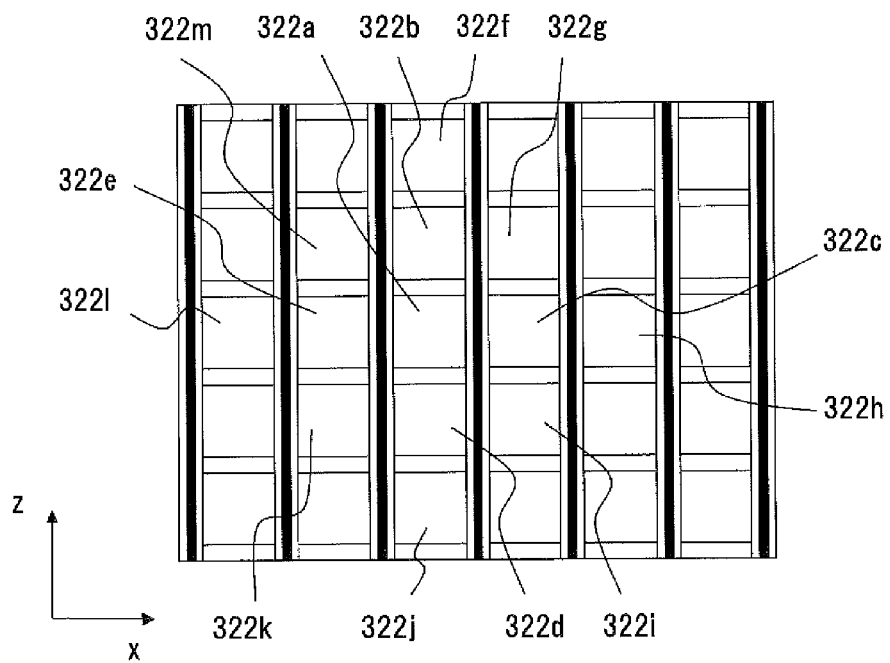

FIGS. 2A and 2B are schematic views showing enlarged portions of the X-ray detector 320, where FIG. 2A is a cross-sectional view taken along a plane parallel to the x-y plane, and FIG. 2B is a top view of the X-ray detector 320 arranged on the x-z plane as seen from the top in the y-direction. Here, the x-axis and y-axis (i.e., x-y coordinate system) are fixed to the rotating body 332, and rotate with the rotation of the rotating body 332. In addition, the direction of the z-axis is the same as the Z-direction shown in FIG. 1.

Note that in the following description of the present specification, the direction of the x-axis (x-direction) is often referred to as a channel direction, and so is the direction of the z-axis (z-direction) as a body axis direction.

As shown in FIG. 2A, the X-ray detector 320 includes multiple X-ray detecting elements 322. Each X-ray detecting element 322 is configured to include a scintillator 325 that emits fluorescence in response to radiation of X-rays, and a photodiode 326 that converts photons such as fluorescence into an electrical signal.

The multiple X-ray detecting elements 322 are arranged in substantially equal intervals in the x-direction, and are separated from each other by a separator 327 composed of a reflective material or the like. Note that the size of the X-ray detecting elements 322 is, for example, 1 mm in the channel direction.

In addition, in FIG. 2A, X-rays which have passed through the subject 500 are radiated from above, and the direction of the X-rays which come incident to each of the scintillators 325 is aligned by a collimator 328. These separators 327 and collimators 328 are used for detection signals not leaking to the X-ray detecting elements 322 which are adjacent to each other, and for removing scattered X-rays which are scattered in the respective scintillators 325.

It should be noted that the X-ray detecting element 322 is not limited to the combination of the scintillator 325 and the photodiode 326, and may be a semiconductor of X-ray detecting element. However, in this case, the separator 327 is often a gap or an insulating material.

Next, as shown in FIG. 2B, the X-ray detecting elements 322 shown with reference numerals 322a, 322b, 322c, 322d, 322e, 322f, 322g, 322h, 322i, 322j, 322k, 322l are arranged in an array on the x-z plane. In FIG. 2B, the number of arrays is a 6 (x-direction)×5 (z-direction), but practically, may be, for example, 1000 (x-direction)×64 (z-direction), and the like.

It should be noted that these multiple X-ray detecting elements 322 arranged in an array may be arranged, more precisely, not on the x-y plane but at positions on an arc which is curved along the rotating body 332 in an annular shape and at the same distance from a point of the X-ray tube 311 where X-rays are generated.

However, it is not always easy to manufacture the X-ray detector 320 having a large number (e.g., 1000) of X-ray detecting elements 322 arranged on the arc. Therefore, in order to facilitate to manufacture the X-ray detector 320, arranging a large number of X-ray detecting elements 322 on an approximate arc is also often performed.

In this case, for example, two-hundred X-ray detector modules in a planar shape may be manufactured, each of which is, for example, arranged with fifty X-ray detecting elements 322 in the channel direction, and the two-hundred X-ray detector modules in a planar shape may be arranged respectively on an arc that is at the same distance from a point of the X-ray tube 311 where X-rays are generated.

It should be noted that in FIG. 2B, the X-ray detecting elements 322 arranged at respective positions are denoted by identifying numerals 322a to 322l, respectively, and these numerals will be used in later description.

Here, the description with reference to FIG. 1 is resumed. In the X-ray CT apparatus 100 shown in FIG. 1, the user is allowed, through the operation terminal 200, to set a time required for the rotating body 332 equipped with the X-ray tube 311 and X-ray detector 320 to rotate once. Then, in the present embodiment, the time required for the rotating body 332 to rotate once may be 1.0 sec per rotation. Also, when the rotating body 332 rotates once, the number of times the X-ray apparatus 300 scans the subject 500 may be 900 times. That is, one scanning may be made every time the rotating body 332 rotates by 0.4 degrees. Note that the required time for the rotating body 332 to rotate and the number of scanning times are not limited to these values, and can be changed as appropriate by the user via the operation terminal 200.

Here, a scanning in the X-ray apparatus 300 refers to X-rays being radiated from the X-ray tube 311 and the intensity of the X-rays which have passed through the subject 500 being detected in the respective X-ray detecting elements 322 that constitute the X-ray detector 320. Data of the intensity of the X-rays detected by the respective X-ray detecting elements 322 is transmitted as scan data via the scanning control unit 340 and the communication line 600 to the image generator 400.

<Configuration of Image Generator 400>

As shown in FIG. 1, the image generator 400 is configured to include a data collecting device 410, a data processing device 420, a display device 430, or the like.

The data collecting device 410 is also often referred to as a DAS (Data Acquisition System), and here, mainly performs processing to receive scan data transmitted via the communication line 600 from the X-ray apparatus 300 and to transfer the scan data received to the data processing device 420.

The data processing device 420 is configured to include a CPU (Central Processing Unit) 421, a memory 422, an HDD (Hard disk drive) 423, and the like. The CPU 421 executes a predefined program stored in the memory 422 or the HDD 423 to implement various processes to be performed by the image generator 400, such as a correction process of the scan data and a generation process of an X-ray CT image.

The display device 430 is composed of an LCD (Liquid Crystal Display) or the like to suitably display the X-ray CT image of the subject 500 generated by the generation process of the X-ray CT image by the CPU 421.

<Configuration of Operation Terminal 200>

The operation terminal 200 is used for the operator entering scanning conditions of the subject 500 and the like, and configured to include a data processing device 210, a keyboard 211, a mouse 212, a display device 213, and the like.

The data processing device 210 has a similar configuration to a common personal computer including a CPU, a memory, an HDD and the like, and the keyboard 211 and the mouse 212 are used as input devices thereof. In addition, the display device 213 is composed of an LCD or the like and can be the one that further includes a touch panel sensor having an input function.

It should be noted that the operation terminal 200 and the image generator 400 may not always be integrally configurated with the X-ray apparatus 300, but may be the one that is provided in another room or at a remote place via a communication line 600 configured with a LAN (Local Area Network), the Internet, or the like.

In addition, the operation terminal 200 and the image generator 400 may be configured as one device using a personal computer or a workstation.

<Procedure of Imaging Process of X-Ray CT Image>

Figure 3:
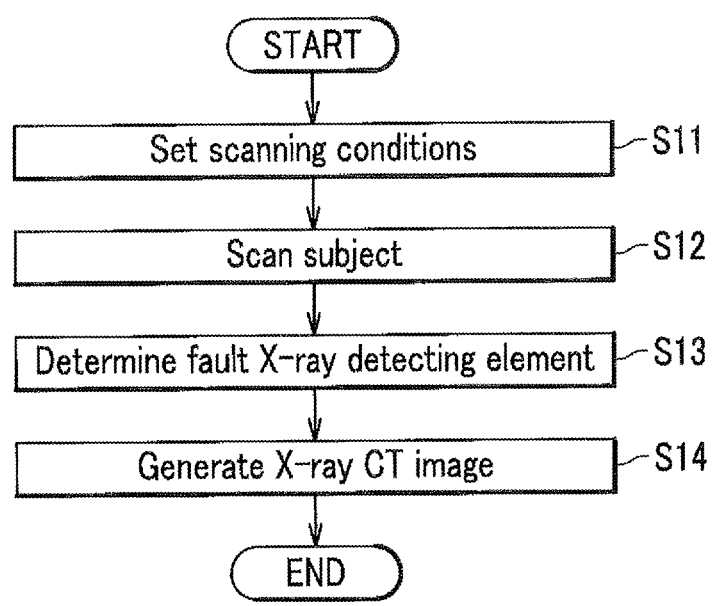
FIG. 3 is a chart showing an exemplary procedure of an imaging process for an X-ray CT image in the X-ray CT apparatus.

FIG. 3 is a chart showing an exemplary procedure of imaging process of an X-ray CT image in the X-ray CT apparatus 100. Note that here, imaging refers to obtaining a two-dimensional tomographic image or a three-dimensional image of the subject 500 as an X-ray CT image based on the scan data obtained by scanning the subject 500 in the X-ray apparatus 300.

As shown in FIG. 3, the procedure of the imaging process of an X-ray CT image includes steps of setting scanning conditions (step S11), scanning the subject 500 (step S12), determining a fault X-ray detecting element 322 (step S13), and generating an X-ray CT image (step S14). Hereinafter, processing in each step will be described in detail.

[Setting Scanning Conditions: Step S11]

Setting scanning conditions in step S11 is performed by the operation terminal 200. Once the user starts the imaging process of an X-ray CT image in the operation terminal 200, the data processing device 210 in the operation terminal 200 displays an imaging condition setting screen (not shown) on the display device 213. Then, the user operates the mouse 212 and the keyboard 211, the touch panel sensor provided to the display device 213, or the like to input data to be set for imaging conditions displayed on the imaging condition setting screen.

The imaging conditions that can be set in the imaging condition setting screen include, for example, a tube current or a tube voltage of the X-ray tube 311, an imaging range of the subject 500, and a time required for the rotating body 332 equipped with the X-ray tube 311 and the X-ray detector 320 to rotate once.

It should be noted that when the data of scanning conditions is set, the data of the scanning conditions that has been set may be stored in the HDD or the like. In that case, as the user can retrieve from the HDD and use the stored data of the scanning conditions, the user may be saved from inputting the data of scanning conditions at every scanning.

[Scanning the Subject: Step S12]

Next, when the user instructs to start scanning the subject 500, the data processing device 210 transmits the data of scanning conditions that has been set to the overall controller 345 of the scanning control unit 340 in the X-ray apparatus 300.

The overall controller 345 of the scanning control unit 340 directs movement, of the subject table 501 on which the subject 500 is placed, according to the data of the scanning conditions, through the table controller 343, toward the direction to be inserted into the bore 331 of the rotating body 332, and further directs the movement to be stopped at a position corresponding to the imaging range set by the same data of the scanning conditions. This completes arranging the subject 500.

In addition, on the other hand, the overall controller 345 directs, via the gantry controller 342, starting the rotation of the drive motor of the rotating body 332 to start the rotation of the rotating body 332. Then, when the rotation of the rotating body 332 reaches a constant speed and arranging the subject 500 is completed, the overall controller 345, based on the data of scanning conditions that has been received, specifies timing of radiating X-rays from the X-ray tube 311 for the X-ray generation controller 341, and also specifies timing of scanning by the X-ray detector 320 for the X-ray detector controller 344.

Then, when the overall controller 345 instructs to start scanning, the X-ray generation controller 341 directs the X-ray tube 311 to operate under conditions of a tube voltage amount and a tube current amount which are specified for each specified timing to x-irradiate the subject 500. Further, on the other hand, the X-ray detector controller 344, for each specified timing, detects the intensity of the X-rays received.

The scanning control unit 340 repeats these operations similarly until the scanning is finished for the imaging range specified in the scanning conditions, to scan the entire imaging range of the subject 500. Then, scan data of the subject 500 that has been scanned (data of the intensity of X-rays detected by each X-ray detecting element 322 for each scanning timing) is transmitted from the scanning control unit 340 via the communication line 600 to the image generator 400 and stored in the HDD 423 of the data processing device 420, or the like.

It should be noted that in the present embodiment, when the subject 500 is scanned, the subject table 501 is repeatedly moved and stopped as appropriate, in synchronization with the timing of scanning, but instead the subject 500 may be scanned while moving the subject table 501 like a so-called helical scan.

[Determining Fault X-Ray Detecting Element: Step S13]

In the present embodiment, the X-ray detector 320 may include a fault X-ray detecting elements 322a. For example, in FIG. 2B, an X-ray detecting element 322a may be faulty to output anomalous values from the X-ray detecting elements 322a. In addition, other X-ray detecting elements 322 may be normal to output normal values from these X-ray detecting elements 322.

There are several methods for determining a fault X-ray detecting element 322a. The methods include determining a fault X-ray detecting element 322a before the scanning, determining a fault X-ray detecting element 322a based on scan data after the scanning to allow a failure even during scanning to be covered, and the like.

In the method for detecting a fault X-ray detecting element 322a before the scanning, for example, a scene in the absence of the subject 500 may be scanned to determine whether or not the scan data has changed significantly as compared with previous scan data of the scene in the absence of the subject 500, and if there is any X-ray detecting element 322 having its scan data changed significantly, this X-ray detecting element 322 is determined to be faulty.

Also, in the method for determining a fault X-ray detecting element 322a based on scan data after the scanning, if there is an X-ray detecting element 322 having its scan data fixed to a certain value, such as remaining to be "0," without any change during scanning the subject 500, or if the scan data after the scanning becomes larger than the scan data of the scene in the absence of the subject 500 (that is, the intensity of X-rays which have passed through the subject 500 is larger than the intensity of X-rays when there is no subject 500), that X-ray detecting element 322 is determined to be faulty.

A process of determining a fault X-ray detecting element 322a, as described above, is executed by the data processing device 420 of the image generator 400. Then, the identification number of the X-ray detecting device 322, which is determined to be faulty through the execution, is registered in a predetermined area of the HDD 423 in the data processing device 420.

It should be noted that in the following description, the X-ray detecting element 322, which is determined to be faulty to have its identification number registered in the HDD 423, may be sometimes referred to as a registered fault X-ray detecting element. In the present embodiment, the identification numbers of such registered fault X-ray detecting elements may be registered multiple in number, for example, up to ten.

In addition, the registered fault X-ray detecting element, which is once determined to be faulty and registered in the HDD 423, may remain registered until the failure is fixed.

Figure 4:
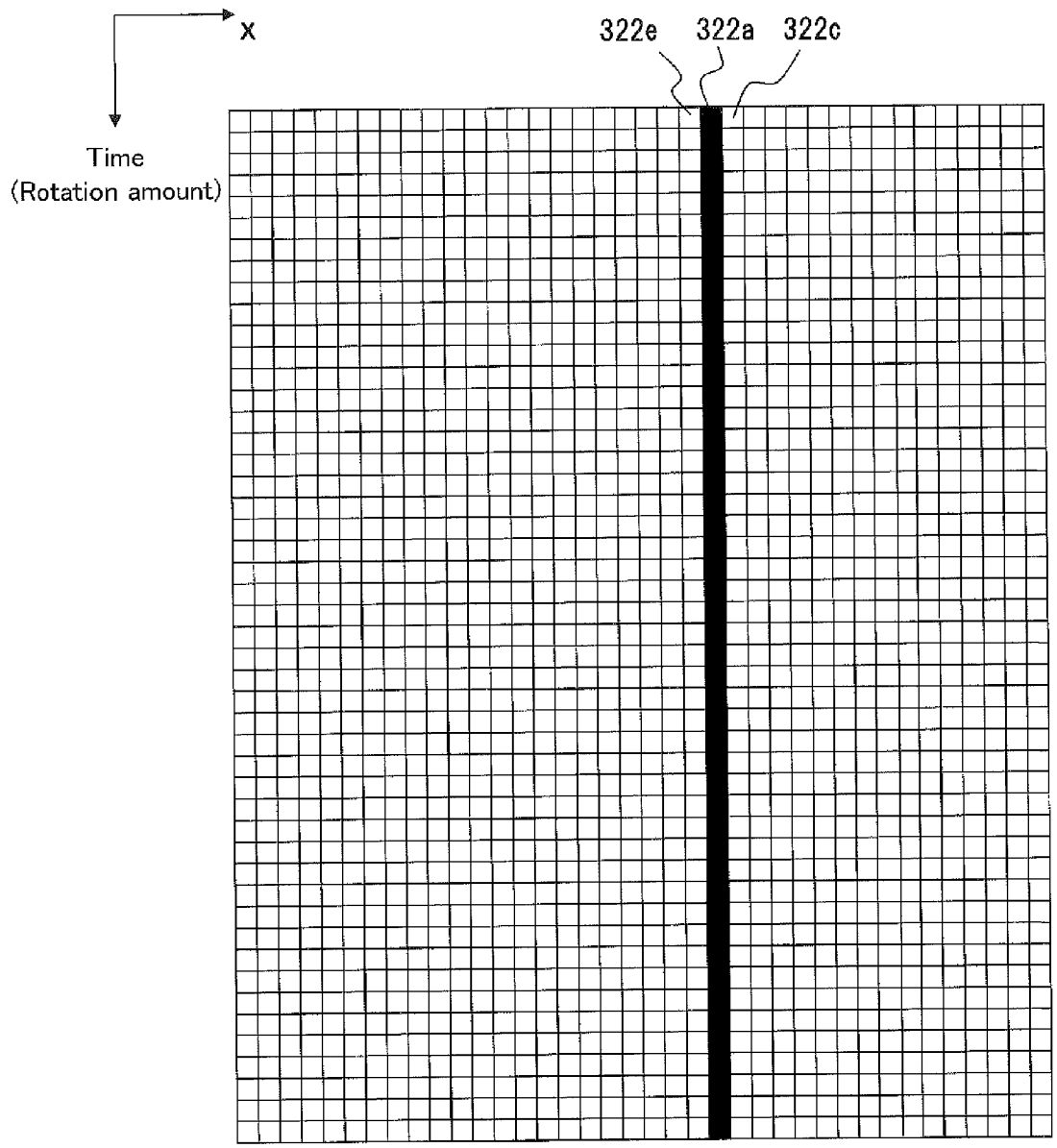
FIG. 4 is a diagram schematically showing arraying of scan data obtained by the X-ray detector.

FIG. 4 is a diagram schematically showing arraying of scan data obtained by the X-ray detector 320. In FIG. 4, data in each column of one row in the horizontal direction represents scan data obtained, in the array structure of the X-ray detecting elements 322 that constitute the X-ray detector 320, from the X-ray detecting elements 322 which are arranged at respective positions in the x-direction belonging to a row in the z-direction (body axis direction). Also, each column in the vertical direction represents scan data obtained from the same X-ray detection elements 322 every time the rotating body 332 rotates by a predetermined angle (e.g., 0.4 degrees, or about 1.1 seconds on a time scale). That is, each column in the vertical direction represents the temporal change of the scan data of the X-ray detecting element 322 which is arranged at each position in the x-direction belonging to a row in the z-direction.

Further, in FIG. 4, white columns represents normal scan data, while a black column represents anomalous scan data. For example, if the X-ray detecting elements 322a in FIG. 3B fails, in FIG. 4, the scan data of the fault X-ray detecting element 322a continues to have an anomalous value (black grids) during the scanning process. Also, in this case, the scan data of the X-ray detecting elements 322e, 322c, which are adjacent in the x-direction to the fault X-ray detecting element 322a, have normal values (white columns).

[Generating X-Ray CT Image: Step S14]

Figure 5:
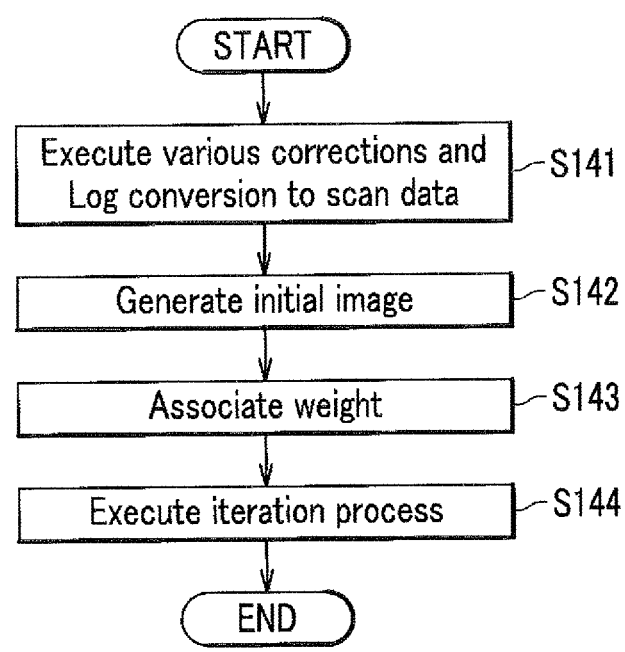
FIG. 5 is a chart showing an example of a detailed process flow of an X-ray CT image-generating process.

FIG. 5 is a chart showing an example of a detailed process flow of an X-ray CT image-generating process. Note that this process is executed by the CPU 421 of the data processing device 420, and at the beginning of its execution, due to processing up to step S13 (see FIG. 3), scan data obtained from the respective X-ray detecting elements 322 for the subject 500 and the identification number(s) of the registered fault X-ray detecting element(s) may be already stored in the HDD 423.

At first, the CPU 421 executes various corrections and a Log conversion to the scan data of the subject 500 stored in the HDD 423 (step S141). Here, the various corrections include a correction based on a known offset correction, and further include a correction to replace the anomalous value of the scan data of the registered fault X-ray detecting element with a mean value of the scan data of the X-ray detecting elements 322 around the registered fault X-ray detecting element, or the like.

Note that in the following description, the scan data subjected to various corrections and a Log conversion may be referred to as corrected scan data.

Here, the reason to correct the anomalous value of the scan data of the registered fault X-ray detecting element is because, if the anomalous value is used as it is, in a subsequent initial image generating process, to generate an initial image, a strong artifact may be caused in the initial image. Then, it is intended to suppress the strong artifact from being caused.

Next, the CPU 421 uses the corrected scan data to generate the initial image for the subsequent iteration process (step S142). As the iteration process repeats a correction of image based on the initial image to generate a final image, the initial image closer to the final image converges faster.

Next, the CPU 421 associates a weight with each corrected scan data (step S143). Here, the corrected scan data of the X-ray detecting elements 322 adjacent to the registered fault X-ray detecting element (hereinafter, referred to as adjacent fault X-ray detecting elements) may be associated with a weight greater than "1", and the corrected scan data of the X-ray detecting elements 322 other than the adjacent fault X-ray detecting elements may be associated with a weight of "1".

In the example of FIG. 2B, the corrected scan data of the adjacent fault X-ray detecting elements 322b, 322c, 322d, 322e adjacent to the fault X-ray detecting element 322a is, for example, associated with a weight of "5," and the corrected scan data of other X-ray detecting elements 322 are associated with a weight of the weight value "1." Here, the weight associated with the corrected scan data of the adjacent fault X-ray detecting elements is not limited to "5," then may be "4," "3," or "6," and is not limited to integers. However, if the weight is too large, pixel data to be obtained may not converge in the next iteration process but diverge. Therefore, it should be noted.

It should be noted that here, as shown in FIG. 2B, with respect to the fault X-ray detecting element 322a, not only the corrected scan data of the adjacent fault X-ray detecting elements 322c, 322e adjacent thereto in the channel direction (x-direction) but also the corrected scan data of the adjacent fault X-ray detecting elements 322b, 322d adjacent thereto in the body axis direction (z-direction) are associated with a weight greater than "1." However, the effect of associating the weight with the corrected scan data can be obtained only by associating the weight with the corrected scan data of the adjacent fault X-ray detecting elements 322c, 322e adjacent in the channel direction (x-direction) to the fault X-ray detecting element 322a. Therefore, those X-ray detecting elements 322, the corrected scan data of which is associated with a weight greater than "1," may be limited to the adjacent fault X-ray detecting elements 322c, 322e adjacent in the channel direction (x-direction) to the fault X-ray detecting element 322a.

In addition, as can be seen from the description of FIG. 2B above, in the present specification, X-ray detecting elements 322 adjacent to a fault X-ray detecting element 322 may only refer to the X-ray detecting elements 322 adjacent thereto in the horizontal direction, but may not refer to the X-ray detecting elements 322 adjacent thereto in the oblique direction.

Further, a weight value "w" is a relative value to each other, and for example, the corrected scan data of the adjacent fault X-ray detecting elements may be associated with a weight of "2.5" and the corrected scan data of the X-ray detecting elements 322 other than the adjacent fault X-ray detecting elements may be associated with a weight of "0.5."

Next, the CPU 421 executes the iteration process (step S144). As for the iteration process, a description will be given in detail as follows, with reference to FIG. 6.

Figure 6:
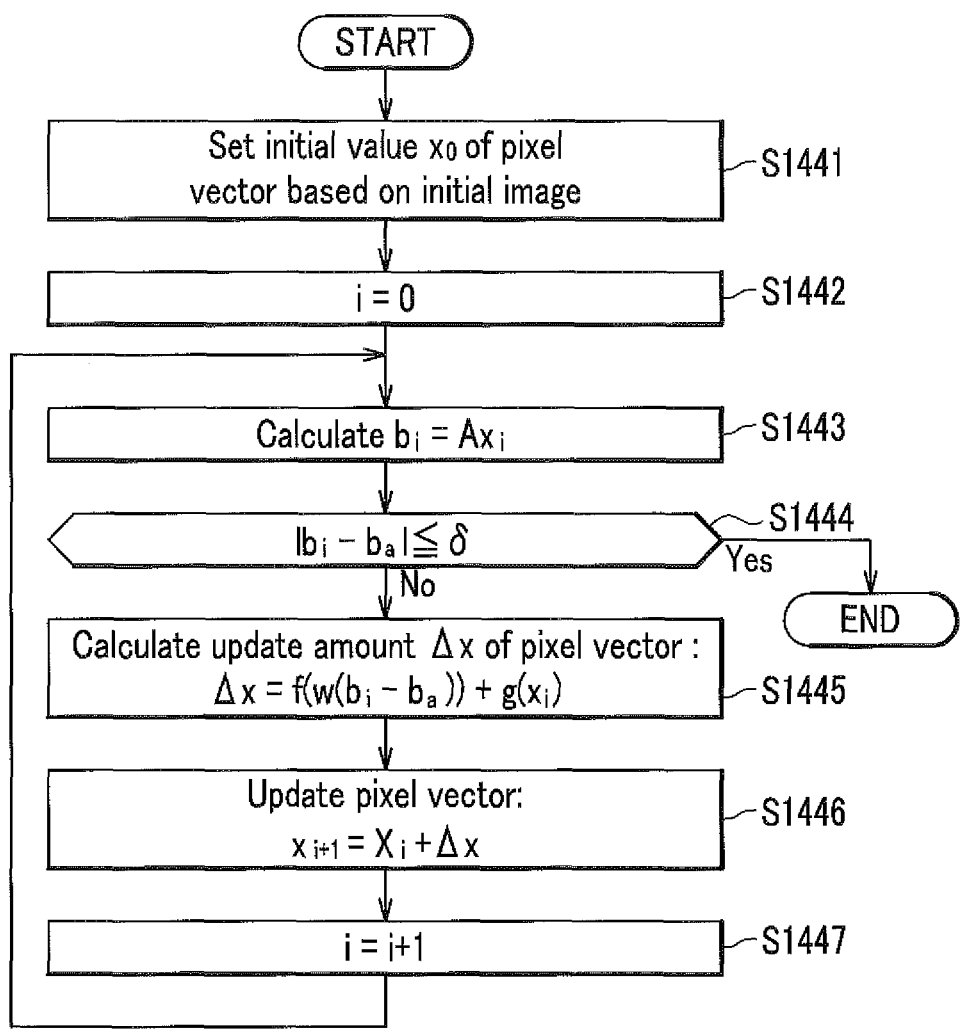
FIG. 6 is a chart showing an example of a detailed process flow of an iteration process.

FIG. 6 is a chart showing an example of a detailed process flow of the iteration process. The CPU 421 at first sets an initial value $x_0$ of a pixel vector x (step S1441). Here, the pixel vector x is a vector composed of pixel data of each pixel of the X-ray CT image to be displayed. In this case, if the X-ray CT image to be displayed, for example, has pixels of 256×256, the pixel vector x will be a vector of 256× 256=65,536 dimensions.

It should be noted that the initial value $x_0$ of the pixel vector x can be generally any data, but the closer image represented by its initial value $x_0$ (hereinafter referred to as an initial image) is to the final image, the faster it converges. In the present embodiment, the initial value $x_0$ is based on the initial image generated in step S142 of FIG. 5.

Next, the CPU 421 initializes a repeating index variable i, i.e., rendering i=0 (step S1442).

Here, a scan data vector h will be explained. The scan data vector b is a vector composed of all the scan data which is detected (scanned) by each X-ray detecting element 322 when an X-ray CT image of a subject 500 is obtained. Note that the term "scan data" here is corrected scan data (also in the following description).

For example, assuming that the X-ray detector 320 is composed of 64×1,000 units of the X-ray detecting elements 322, and that while the rotating body 332 equipped with the X-ray detector 320 rotates once, X-rays are radiated from the X-ray tube 311 every time the rotating body rotates by 0.4 degrees and the intensity of X-rays which have passed through the subject 500 is detected (scanned) by each X-ray detecting element 322, the number of all the scan data by respective X-ray detection elements 322 will be 64×1,000× 900=57,600,000. Thus, the scan data vector b is a 57,600, 000-dimensional vector.

Next, a projection matrix A will be described. The projection matrix A is a matrix to link the pixel vector x and the scan data vector b, having a relationship:

$$Ax=b \qquad \text{Equation (1)}.$$

Here, for example, if the pixel vector x is 65,536-dimensional and the scan data vector b is 57,600,000-dimensional, the projection matrix A becomes a matrix of 57,600,000 rows×65,536 columns. The value of an element $a_{ij}$ of the projection matrix A is a constant defined with the position of the X-ray tube 311, the position of each X-ray detecting element 322, the display position and the way to be displayed of the subject 500, and the like. In the present embodiment, the value of the element $a_{ij}$ of the projection matrix A may be stored in advance in the HDD 423. Note that the projection matrix A is known to be generally a sparse matrix in which many elements have the value of "0."

Then, the CPU 421, for an index variable i at that time, using the pixel vector $x_i$ that has been obtained by that time, calculates the scan data vector $b_i$ according to equation (1), i.e., calculates $b_i=Ax_i$ (step S1443). The scan data vector $b_i$ obtained in this way can be said as a scan data vector calculated in the iteration process from the pixel vector $x_i$ that has been obtained by that time.

On the other hand, the scan data vector b actually obtained by the X-ray detecting element 322 may be represented in particular as $b_a$. In the present embodiment, the scan data vector $b_a$ actually obtained means the one that is created based on the corrected scan data obtained in step S141 of FIG. 5.

Next, the CPU 421 obtains the magnitude (absolute value) of a difference vector between the scan data vector $b_i$ calculated from the pixel vector $x_i$ and the scan data vector $b_a$ actually obtained, namely, $|b_i-b_a|$, and determines whether that $|b_i-b_a|$ has become smaller than a predetermined threshold value δ (step S1444).

As a result of the determination, if the magnitude of the difference vector $|b_i-b_a|$ is not yet smaller than the threshold value δ, the CPU 421 calculates an update amount Δx of the pixel vector $x_i$ (step S1445). As a method for calculating the update amount Δx of the pixel vector $x_i$ in the iteration process, there can be various methods such as ML-EM (Maximum Likelihood-Expectation Maximization) method, but here, the calculation method may not be limited to a specific one.

Therefore, here, the update amount Δx of the pixel vector $x_i$ may be expressed as $$\Delta x = F(w(b_i - b_a)) + G(x_i) \qquad \text{Equation (2)}.$$

Note that w represents a weight associated with each element of the scan data vector ba, and F, G are functions, each having a vector as a variable.

Next, the CPU 421 updates the pixel vector $x_i$ using the update amount Δx of the pixel vector $x_i$ to calculate the pixel vector $x_{i+1}$ for use in the next iterative operation. In other words, $x_{i+1} = x_i + \Delta x$ is calculated (step S1446).

Next, the CPU 421 counts up the value of the index variable i by one, that is, to render i=i+1 (step S1447), and returns to step S1443 to repeatedly perform processing in step S1443 and steps thereafter.

In addition, in the determination of step S1444, if the magnitude of the difference vector $|b_i-b_a|$ has become smaller than the threshold value δ, the CPU 421 ends the iteration process, and renders the pixel vector $x_i$ obtained by that time as a pixel vector $x_f$ of the final image. That is, the display unit 430 is displayed with the final image based on this pixel vector $x_f$ as an X-ray CT image of the subject 500.

Data of the pixel vector $x_f$ obtained by the above process is stored in the HDD 423. Therefore, the CPU 421, at any time in response to a request from the user, can display the final image based on the pixel vector $x_f$ on the display device 430, or on the display device 213 of the operation terminal 200.

It should be noted that in the iteration process described above, processing in steps S1143 to S1147 is a process constituting a unit of iteration, and this process constituting a unit of iteration, that is, a process of one iteration will be referred to as an iterative operation in the following description.

Further, in the iteration process described above, the end of the iteration in the iteration process is determined by the magnitude of the difference vector |bi−ba| becoming smaller than the threshold value δ, but the determination of the end of the iteration is not limited thereto. For example, the number of iterations (i.e., index variable i) exceeding a certain number, or the like may be used to determine the end of the iteration.

<Advantageous Effects>

Here, a description will be given of effects of the present embodiment. A comparative example may be a method of iteration described in Japanese Patent Application Publication No. 2008-245695. A difference between the two is as follows.

(1) In the method of iteration described in Japanese Patent Application Publication No. 2008-245695, detected data obtained from a fault X-ray detecting element 322 is not used in the iterative operation.

(2) In the present embodiment, the detected data (corrected scan data) obtained from the fault X-ray detecting element 322a may be used in principle, to associate a weight greater than "1" with detected data (corrected scan data) obtained from the adjacent fault X-ray detecting elements adjacent to the fault X-ray detecting element 322a, and to reflect the weight when calculating the update amount Δx of the pixel vector $x_i$ in the iterative operation.

Due to this difference between the two, advantageous effects can be obtained such that the convergence rate of iteration according to the present embodiment becomes faster than the convergence rate of iteration described in Japanese Patent Application Publication No. 2008-245695. This is based on that the iteration process to obtain an X-ray CT image is a process to statistically obtain pixel data that matches most with scan data actually obtained (i.e., corrected scan data: hereinafter in the description of this advantageous effects, simply referred to as scan data).

That is, the pixel data that matches most with the scan data actually obtained is nothing but obtaining $x_i = x_a$ so as $|\Delta x_i - b_a|$ to become minimal, in terms of the symbols used in the description of the process flow in FIG. 6. In the present embodiment, as described above, since the dimension of the $b_a$ is much greater than that of the $x_i$, the $x_i$ is defined depending on the statistical value of the $b_a$. Note that the $x_a$ is often referred to as a likelihood value of the pixel data, and the likelihood value $x_a$ corresponds to the pixel vector $x_f$ of the final image obtained through the iteration process described in FIG. 6.

Now, here, if a fault X-ray detecting element 322a exists in the X-ray detector 320, the scan data $b_a$ obtained from the fault X-ray detecting element 322a becomes an anomalous value. In this case, an X-ray absorption rate of the subject 500 cannot be obtained on a line connecting the X-ray tube 311 and this fault X-ray detecting element 322a.

However, in the present embodiment, scanning of the subject 500 is performed while rotating the X-ray tube 311 as well as the multiple X-ray detecting elements 322 that are arranged in an array, for example, 900 times per second.

Therefore, even if the X-ray absorption rate of the subject 500 cannot be obtained at a certain scanning timing on a line 510 connecting the X-ray tube 311 and the fault X-ray detecting element 322a, a line (not shown) connecting the X-ray tube 311 and an X-ray detecting element 322, which is adjacent, backward or forward, to the fault X-ray detecting element 322a, will be a line extremely approximated to the line 510 at a scanning timing before or after the above-mentioned timing. Thus, for an X-ray absorption rate of the subject 500 on the line 510 which cannot be obtained at a certain scanning timing, an approximated value having high accuracy may be obtained at a scanning timing before and after the above-mentioned timing by the X-ray detecting elements 322 adjacent to the fault X-ray detecting element 322a.

This will be briefly described as follows by using FIG. 11.

At a certain scanning timing, the fault X-ray detecting element 322a cannot obtain an X-ray absorption rate of the subject 500 on the line 510 connecting the X-ray tube 311 and the fault X-ray detecting element 322a. However, at the next scanning timing where the positions of the X-ray tube 311 as well as the X-ray detecting element 322a are slightly rotated, a line connecting the X-ray tube 311 and the X-ray detecting element 322e adjacent to the X-ray detection element 322 will be a line extremely approximated to the line 510. Also, similarly, at the previous scanning timing where the positions of the X-ray tube 311 as well as the X-ray detecting element 322a are slightly rotated in the reverse direction, a line connecting the X-ray tube 311 and the X-ray detecting element 322c adjacent to the X-ray detection element 322 has been a line extremely approximated to the line 510.

Therefore, for an X-ray absorption rate of the subject 500 on the line 510 which has failed to be obtained at a certain scanning timing, an approximated value having high accuracy can be obtained by the X-ray detecting elements 322c, 322e at scanning timings before and after the above-mentioned timing. Note that the X-ray absorption rate referred to in the above description corresponds to the pixel data.

In the above situation, in the present embodiment, the scan data obtained from the X-ray detecting elements 322 (322c, 322e) adjacent to the fault X-ray detecting element 322a is associated with a weight greater than "1," such as "5," and the iteration process is performed afterward. In this case, the update amount for the pixel data of the pixel on the line 510, for which the pixel data has not been obtained at a certain scanning timing because of the fault X-ray detecting element 322a, is larger than an update amount for the other pixel data due to the weight greater than "1" associated with the scan data obtained from the X-ray detecting elements 322 adjacent to the fault X-ray detecting element 322a.

On the other hand, in the invention described in Japanese Patent Application Publication No. 2008-245695, since the scan data obtained from the X-ray detecting elements 322 adjacent to the fault X-ray detecting element 322a remains deficient, and yet the update amount for the pixel data of the pixel on the line 510 does not reflect data such as a weight, the update amount is substantially smaller than the update amount for the other pixel data.

Therefore, the time in which the pixel vector x converges to the likelihood value $x_a$ becomes shorter in the present embodiment than in the invention described in Japanese Patent Application Publication No. 2008-245695 for the update amount reflecting the weight.

Incidentally, according to the simulation experiments of the present inventors, if the scan data obtained by the fault X-ray detecting element 322a is not used, as in the invention described in Japanese Patent Application Publication No. 2008-245695, an artifact caused by the initial image was eliminated only after repeating the iterative operation about 25 times. On the other hand, if the scan data obtained from the X-ray detecting elements 322 adjacent to the fault X-ray detecting element 322a was associated with a weight of "3" to "4" and the calculation of update amount reflected the weight, as described in the present embodiment, an artifact was found to be eliminated around seven to ten times.

As described above, according to the present embodiment, if the fault X-ray detecting element 322a exists in the X-ray detector 320, a convergence time of repeated iterative operation when generating an X-ray CT image can be made shorter, that is, the convergence speed can be made faster, as compared with the prior art. Thus, in the present embodiment, an artifact of the X-ray CT image, which is caused if a fault X-ray detecting element 322a exists, can be eliminated more reliably and faster. As a result, the reliability of the X-ray CT image to be generated can be improved.

Modification 1 of First Embodiment

Figure 7:
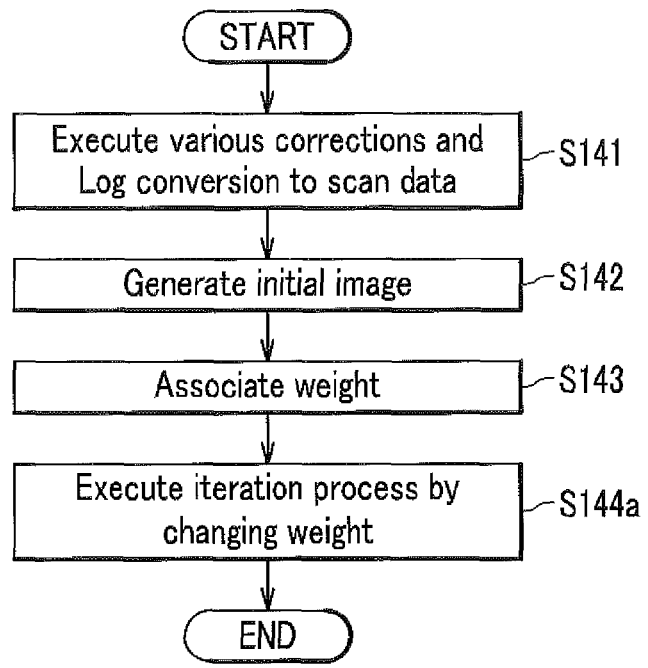
FIG. 7 is a chart showing an exemplary procedure of the imaging process for an X-ray CT image in a first modification of the first embodiment of the present invention.

FIG. 7 is a chart showing an exemplary procedure of the imaging process of an X-ray CT image in a modification 1 of the first embodiment. As shown in FIG. 7, the procedure of the imaging process of an X-ray CT image in the modification 1 is nothing but a part of the process of generating the X-ray CT image in the first embodiment shown in FIG. 5 being modified. That is, the processing in the modification 1 is the same as the first embodiment from step S141 to step S143, and only step S144a is different.

In the present modification, the CPU 421, in the same manner as in the first embodiment, associates a weight with the corrected scan data of each X-ray detecting element (step S143), then executes an iteration process by changing the weight associated with the corrected scan data of the adjacent fault X-ray detecting elements (step S144a).

Here, the specific way of changing the weight in the iteration process is, for example, when performing a first iterative operation, the weight of, for example, "5," associated with the corrected scan data of the adjacent fault X-ray detecting elements is used as-is in step S143, and when performing a second iterative operation and later, the weight is decreased by "1" sequentially as "4," "3," "2," "1," leaving the weight as "1" for the sixth operation and later.

It should be noted that the way of decreasing the weight is not limited to decreasing it by "1" for each iterative operation, but the weight may be decreased, for example, exponentially for every iterative operation, or the weight may be decreased in geometrical progression by multiplying, for example, 0.9, for every iterative operation.

In this way, the weight associated with the corrected scan data of the adjacent fault X-ray detecting elements may be decreased for every iterative operation to render the time to converge even shorter than in the first embodiment and to avoid a risk of not converging, such as fluctuation or divergence.

Modification 2 of First Embodiment

In the first embodiment and the modification 1 of the first embodiment as described above, only the corrected scan data of the adjacent fault X-ray detecting elements adjacent to the fault X-ray detecting element 322a is associated with a weight greater than or equal to "1." In contrast, in the present modification, the corrected scan data of not only the adjacent fault X-ray detecting elements but also the X-ray detecting elements further adjacent to the adjacent fault X-ray detecting elements may be associated with a weight greater than or equal to "1." However, the weight associated with the corrected scan data of the X-ray detection elements further adjacent to the adjacent fault X-ray detecting elements may be smaller than the weight associated with the corrected scan data of the adjacent fault X-ray detecting elements.

For example, if the corrected scan data of the adjacent fault X-ray detecting elements is associated with a weight of "4," the corrected scan data of the X-ray detecting elements further adjacent to the adjacent fault X-ray detecting elements may be given a weight of "2." In this way, a sharp change in the weight associated with the corrected scan data of the X-ray detecting elements 322 in the vicinity of the fault X-ray detecting element 322a can be smoothed.

That is, in the example of FIG. 2B, the corrected scan data of four adjacent fault X-ray detecting elements 322b to 322e adjacent to the fault X-ray detecting element 322a is given a weight of "4," and further the corrected scan data of eight X-ray detecting elements 322f to 322m adjacent to these adjacent fault X-ray detecting elements 322b to 322e is given a weight of "2."

For example, in the first embodiment, if only the corrected scan data of the adjacent fault X-ray detecting elements is associated with a large weight, the weight seems protruding from the weight given to the corrected scan data of surrounding adjacent fault X-ray detecting elements. In such a case, there is a difference in the convergence rate between a pixel through which plenty of corrected scan data associated with a large weight passes, and a pixel through which plenty of corrected scan data associated with a small weight passes. As a result, the standard deviation (SD) value for each part of the image changes by each part. When there is a part having a different SD value in the same structure of the subject 500 (e.g., an internal organ if the subject 500 is a human body), the difference between the SD values may sometimes appear to be an artifact.

In the present modification, since even corrected scan data of the X-ray detecting elements 322f to 322m adjacent to the adjacent fault X-ray detecting elements 322b to 322e is associated with a weight smaller than the weight associated with the corrected scan data of the adjacent fault X-ray detecting elements 322b to 322e, the weight associated with the corrected scan data of the X-ray detecting elements 322b to 322m around the fault X-ray detecting element 322a does not change sharply but changes smoothly. Therefore, since the change in the SD value for each part of the image is eased, a change in the SD value for each part of the image is prevented from appearing to be an artifact.

That is, in the present modification, the difference in convergence for each part can be prevented which is caused by a sharp change of a weight. As a result, SD values of the image (noise distribution of the image) can be made seamless to prevent a difference of images caused by the difference of SD values for each part of the image from being incorrectly determined as an artifact.

Modification 3 of First Embodiment

In the first embodiment, the modification 1 of the first embodiment, and the modification 2 of the first embodiment, a weight associated with the corrected scan data of the fault X-ray detecting element 322a itself has not been specifically referred to, and a description has been given so as its weight to be considered as "1."

In general, associating the weight of "1" with the corrected scan data of the fault X-ray detecting element 322a does not cause a big problem. However, when considering the convergence of the iterative operation and the quality of an image obtained by the convergence, in terms of eliminating an influence from the incorrect scan data (anomalous scan data) as much as possible, it is preferred that the weight associated with the corrected scan data of the fault X-ray detecting element 322a be smaller than "1" but greater than or equal to "0."

Therefore, in the present modification, for each of the first embodiment, the modification 1 of the first modification and the modification 2 of the first embodiment, the weight given to the corrected scan data of the fault X-ray detecting element 322a may be smaller than "1" but greater than or equal to "0."

It should be noted that rendering the weight given to the corrected scan data of the fault X-ray detecting element 322a "0" may be an idea corresponding to not using the scan data of the fault X-ray detecting element 322a as is the case in Japanese Patent Application Publication No. 2008-245695. However, Japanese Patent Application Publication No. 2008-245695 does not disclose anything about rendering the weight given to the corrected scan data of the adjacent fault X-ray detecting elements greater than or equal to "1."

In the present modification, the influence from the incorrect scan data of the fault X-ray detecting element 322a becomes smaller to improve the quality of an image obtained by the convergence of the iterative operation Modification 4 of First Embodiment In the first embodiment and its modifications 1 to 3 as described above, it is considered that only one X-ray detecting element 322 fails, however, there may be a case where multiple X-ray detecting elements 322 fail. In the present modification, a description will be given of associating a weight when multiple X-ray detecting elements 322 fail.

Even when multiple X-ray detecting elements 322 fail, if the multiple fault X-ray detecting elements 322 are mutually distant from one another, the fault X-ray detecting elements 322 may be treated in much the same way as in the case of the first embodiment and its modifications 1 to 3. However, if the multiple fault X-ray detecting elements 322 are located closely with one another, the way of treating a fault element in the first embodiment and its modifications 1 to 3 can not be applied as-is.

For example, there may be a case where states of three X-ray detecting elements 322, which are aligned in series in a part of the X-ray detector 320, are faulty, normal, and faulty, respectively, and states of the other X-ray detecting elements 322 are normal. This corresponds to a case in the example of FIG. 2B where X-ray detecting elements 322c and 322e fail and all others are normal.

In this case, if the weighting of the adjacent fault X-ray detecting elements referred to in the first embodiment is applied, in the example of FIG. 2B, seven X-ray detecting elements 322a, 322g, 322h, 322i, 322l, 322k, 322m correspond to the fault adjacent X-ray detecting elements. Also, as for the adjacent fault X-ray detecting element 322a, it will be adjacent to both the fault X-ray detecting elements 322c and 322e.

Here, if a weight associated with the corrected scan data of the adjacent fault X-ray detecting elements has been determined to be, for example, "5," for example, "10" may be associated, by adding "5" and "5," with a weight of the corrected scan data of an X-ray detecting element 322 adjacent to multiple adjacent fault X-ray detecting elements, such as the X-ray detecting element 322a. Alternatively, "25" may be associated by multiplying "5" by "5."

However, as described above, if the weight is too large, the iterative operation may diverge. Therefore, an upper limit value may be provided for the weight, and if a result of the addition or multiplication of the weight exceeds the upper limit value, the upper limit value may be associated as the weight.

For example, if the upper limit value has been set to "8" for the weight, either when two weights are added to be "10" or multiplied to be "25," the upper limit value of "8" is adopted as the weight.

In addition, even for a case where, as in the modification 2 of the first embodiment, not only corrected scan data of the adjacent fault X-ray detecting elements, but also corrected scan data of the X-ray detecting elements 322 adjacent to the adjacent fault X-ray detecting elements are given a weight, the similar way of associating a weight, as described above, may also be applied. Further, in this case, multiple weights may be added or multiplied and when the result is greater than the upper limit value, the upper limit value may be adopted as the weight. Alternatively, among multiple weights, either a larger one or a smaller one may be adopted.

As described above, in the present modification, even if there are multiple fault X-ray detecting elements, the magnitude of the weight can be confined to reduce a risk of divergence in the iterative operation.

Second Embodiment

In the first embodiment, a case is considered where one or more X-ray detecting elements 322 fail fixedly, but in the second embodiment, another case will be considered where an operation of the X-ray tube 311 is unstable to cause the intensity of X-rays radiated from the X-ray tube 311 sharply changing at a certain timing.

Since the configuration of the X-ray CT apparatus 100 is the same as in the case of the first embodiment, a description thereof will be omitted. On the other hand, the procedure of an imaging process for an X-ray CT image in this X-ray CT apparatus 100 is slightly different from that in the first embodiment (see FIG. 3), then the difference will be described below.

<Procedure of Imaging Process for X-Ray CT Image>

Figure 8:
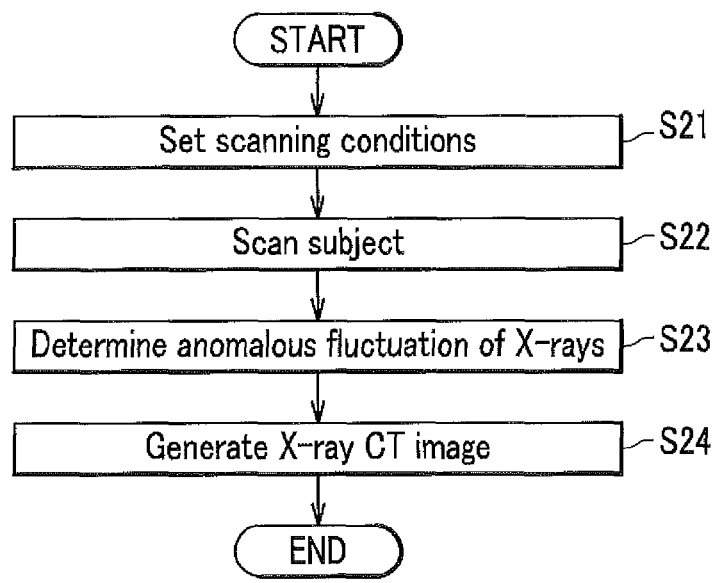
FIG. 8 is a chart showing an exemplary procedure of the imaging process for an X-ray CT image in the X-ray CT apparatus according to a second embodiment of the present invention.

FIG. 8 is a chart showing an exemplary procedure of imaging process for an X-ray CT image in the X-ray CT apparatus 100 according to a second embodiment of the present invention.

As shown in FIG. 8, the procedure of the imaging process of an X-ray CT image is configured to include steps of setting scanning conditions (step S21); scanning the subject 500 (step S22); determining an anomalous fluctuation of X-rays (step S23); and generating an X-ray CT image (step S24).

Among these, setting scanning conditions (step S21) and scanning the subject 500 (step S22) are the same processing as setting scanning conditions (step S11) and scanning the subject 500 (step S12) as shown in FIG. 3, then the description thereof will be omitted and determining an anomalous fluctuation of X-rays (step S23) and processing thereafter will be described.

[Determining Anomalous Fluctuation of X-Rays: Step S23]

As for a way of determining an anomalous fluctuation of X-rays, there is, for example, a way of using a change in the output of X-rays in a referential detecting element to determine an anomalous fluctuation. The referential detecting element referred to here is a detecting element for measuring a change in the output of the X-rays, and is also an X-ray detecting element provided at a position which is not affected by the subject 500, rotates together with the X-ray tube 311, and continues to have the distance from the X-ray tube 311 unchanged during scanning.

Then, in the present embodiment, among the X-ray detecting elements 322 included in the X-ray detector 320, an X-ray detecting element 322 located at an end, where X-rays radiated from the X-ray tube 311 always come incident directly without passing through the subject 500, may be used as a referential detecting element. Thus, the CPU 421 in the data processing device 420 can obtain a detection signal of the referential detecting element as scan data to determine an anomalous fluctuation of X-rays from among the scan data.

That is, since the detection signal (scan data) of the referential detecting element is not affected by the subject 500 to generally remain constant, a change in the detection signal (scan data) may represent a fluctuation of X-rays radiated from the X-ray tube 311. Then, the CPU 421 determines an anomalous fluctuation of X-rays in the following manner.

The CPU 421 at first, based on scan data of the referential detecting element which has been obtained and stored in advance, calculates an average value and a variance σ. Then, if scan data of the referential detecting element obtained during scanning the subject 500 is outside the average value by 3σ or more, it is determined that an anomalous fluctuation of X-rays has occurred at that timing. Then, the CPU 421 determines that scan data of all the other X-ray detecting elements 322 which has been obtained at the timing is anomalous.

Figure 9:
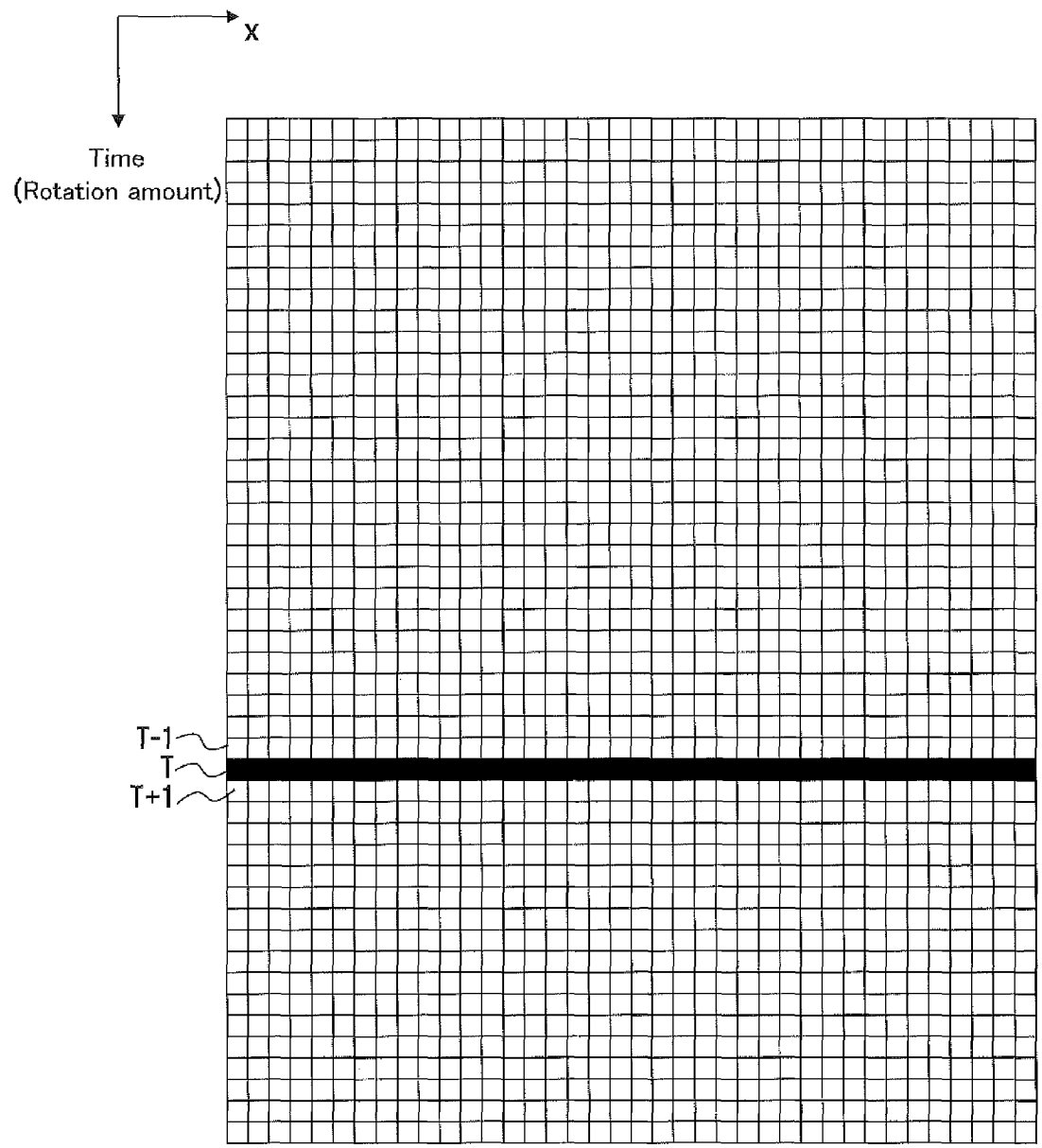
FIG. 9 is a diagram schematically showing arraying of scan data obtained by the X-ray detector and an exemplary timing of an anomalous fluctuation of X-rays.

FIG. 9 is a diagram schematically showing arraying of scan data obtained by the X-ray detector 320 and an exemplary timing of an anomalous fluctuation of X-rays. FIG. 9 indicates that an anomalous fluctuation of X-rays has occurred at a time T, and scan data of the respective X-ray detecting elements 322 at the time T is blacked out.

It should be noted that in the way of determining an anomalous fluctuation as described above, even a fluctuation of the scan data caused by a failure or operational irregularity of the referential detecting element itself may also be detected as an anomalous fluctuation of X-rays. In this case, the scan data obtained from other X-ray detecting elements 322 may be likely normal. Therefore, in order to utilize the scan data which is likely normal, it is preferable to be able to determine that the fluctuation of the scan data is not caused by an anomalous fluctuation of X-rays.

In order to determine whether an anomalous fluctuation of the scan data of the referential detecting element is caused by the X-ray tube 311 or the referential detecting element, multiple referential detecting elements may be provided in the X-ray detector 320. That is, if there are anomalous fluctuations in the scan data of all the multiple referential detecting elements, those anomalous fluctuations can be determined as caused by the X-ray tube 311, and also, if there is no anomalous fluctuation in the scan data of any of the multiple referential detecting elements, the anomalous fluctuation(s) can be determined as caused by the referential detecting element(s).

[Generating X-Ray CT Image: Step S24]

Figure 10:
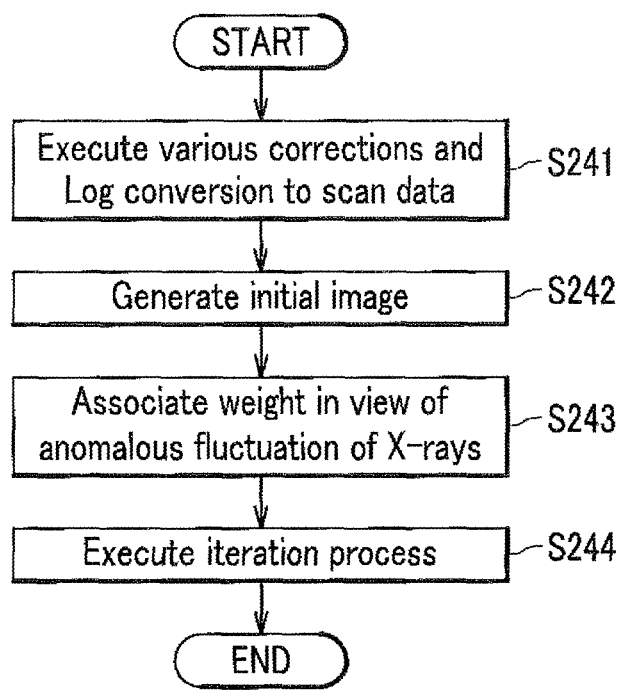
FIG. 10 is a chart showing an example of a detailed process flow of the X-ray CT image-generating process according to a second embodiment of the present invention.

FIG. 10 is a chart showing an example of a detailed process flow of the X-ray CT image-generating process according to the second embodiment of the present invention. Note that this process, as in the first embodiment, is executed by the CPU 421 in the data processing device 420, and at the beginning of its execution, by the processing up to step S23 (see FIG. 8), scan data obtained from respective X-ray detecting elements 322 for the subject 500 and data indicating a time T when an anomalous fluctuation of X-rays has occurred may be already stored in the HDD 423.

At first, the CPU 421 executes various corrections and Log conversion to the scan data of the subject 500 stored in the HDD 423 (step S241). The correction is substantially the same as the correction described in the first embodiment. However, if the scan data obtained at time T, when an anomalous fluctuation of X-rays has occurred, is used as-is to generate an initial image, strong artifacts may be caused in the initial image. Then, a correction may be required such as replacing the scan data in respective columns at time T with average values of other scan data in respective columns.

Note that the scan data, for which corrections and Log conversion are executed as described above, may be referred to as corrected scan data hereinafter.

Next, the CPU 421 generates an initial image (step S242). This is the same as the processing in the first embodiment.

Next, the CPU 421 associates weights in view of an anomalous fluctuation of X-rays (step S243). For example, the scan data (corrected scan data) obtained from the respective X-ray detecting elements 322 at time T−1 and time T+1 before and after the time T, which is determined in step S23 (see FIG. 8) to be a time when an anomalous fluctuation of X-rays has occurred, may be associated with a weight greater than "1" such as "5," while the scan data (corrected scan data) obtained from the respective X-ray detecting elements 322 at other times may be associated with a weight of "1."

Note that further in this case, the scan data (corrected scan data) obtained from the respective X-ray detecting elements 322 at time T−2 and time T+2 may be associated with a weight smaller than the weight of "5," such as "2," which is associated with the scan data (corrected scan data) obtained from the respective X-ray detecting elements 322 at time T−1 and time T+1.

Next, the CPU 421 executes an iteration process as in the first embodiment (step S244) to obtain an X-ray CT image of the subject 500 to be displayed on the display device 430. Note that, in this iteration process, as in the first embodiment, an update amount Δx for the pixel vector is calculated in accordance with Equation (2). Therefore, the update amount Δx of the pixel vector may reflect the weight greater than "1," which is associated with the scan data (corrected scan data) obtained from the respective X-ray detecting elements 322 at time T−1 and time T+1.

It should be noted that in the iterative processing of the iterative operation in step S244, the weight greater than "1," which is associated in step S243 with the scan data (corrected scan data) obtained from the respective X-ray detecting elements 322 at time T−1 and time T+1, may be gradually decreased at every iterative operation until the weight becomes "1."

Hereinabove, according to the second embodiment, artifacts can be prevented from occurring that are caused by an error in the scan data due to a failure or irregularity of the X-ray tube 311 or the reference detector.

Other Embodiment

The first embodiment and the second embodiment may be implemented in combination. In that case, the CPU 421 may execute determining an anomalous fluctuation of X-rays (step S23) before determining a fault X-ray detecting element (step S13), or conversely, may execute determining a fault X-ray detecting element (step S13) before determining an anomalous fluctuation of X-rays (step S23).

In addition, even if there is an error in the scan data obtained from a part of X-ray detecting elements 322 due to not only a failure of an X-ray detecting element 322 or an anomalous fluctuation of X-rays but also some other reason, artifacts caused by the error in the scan data can be removed or reduced by iterative operations which converge in a short time, in the same manner as in the first embodiment or the second embodiment.

Further, in the embodiments described above, by way of an example of a third-generation X-ray CT apparatus 100 in which the X-ray tube 311 and the X-ray detector 320 are rotated together, a way of processing to generate an X-ray CT image, and the like are described, but the description can be used substantially in the same manner for a fourth-generation X-ray CT apparatus in which an X-ray detector is provided at a fixed position, or the like.

It should be noted that the present invention is not limited to the embodiments described above, but further includes various modifications. For example, the embodiments hereinabove have been described in detail in order to better illustrate the present invention, but should not necessarily be limited to those which include all the components as described above. Also, a part of the components of an embodiment may be replaced with a part of the components of another embodiment, and further the components of an embodiment may be added with a part or all of the components of another embodiment.

The invention claimed is:

1. An X-ray CT apparatus comprising:
an X-ray generator that generates X-rays;
an X-ray detector that is configured to have multiple X-ray detecting elements arranged in array for detecting intensity of the X-rays;
a scanning control unit that transmits detection data detected by the X-ray detecting elements as scan data of a subject; and
a data processing device that obtains the scan data transmitted from the scanning control unit, and processes the obtained scan data to generate an X-ray CT image of the subject,
wherein the data processing device executes steps of:
storing the scan data obtained by the X-ray detecting elements into a storage unit in accordance with an arrangement of the X-ray detection elements in the X-ray detector, and detecting anomalous scan data among the stored scan data;
associating a weight with scan data adjacent to the anomalous scan data detected, the weight being greater than a weight associated with other scan data; and
calculating pixel data of the X-ray CT image of the subject, through iteration of an iterative operation using a projection matrix defined by data including a layout position of the X-ray generator and arrangement positions of the respective multiple X-ray detection elements, pixel data that has been set at that time, and the scan data,
wherein in the iterative operation, when calculating an update amount for the pixel data based on difference data between projection data obtained from the projection matrix and the pixel data at that time, and the scan data, the difference data is weighted with the weight associated with the scan data corresponding to the difference data.

2. The X-ray CT apparatus according to claim 1, wherein if the anomalous scan data is caused by a failure of an X-ray detecting element of multiple X-ray detecting elements that constitute the X-ray detector,
the data processing device performs:
a step of associating a weight with scan data obtained from X-ray detecting elements adjacent to the fault X-ray detecting element, the weight being greater than a weight associated with other scan data.

3. The X-ray CT apparatus according to claim 2, wherein the data processing device performs:
a step, when associating a weight with the scan data obtained from the X-ray detecting elements adjacent to the fault X-ray detecting element, of associating a weight, which is greater than a weight associated with the other scan data, with scan data obtained from X-ray detecting elements adjacent in the channel direction to the fault X-ray detecting element.

4. The X-ray CT apparatus according to claim 1, wherein if the anomalous scan data is caused by an anomalous fluctuation of X-rays generated by the X-ray generator,
the data processing device performs:
a step of associating a weight with scan data obtained at a time one unit of time before and after the time when the anomalous fluctuation of X-rays has been detected, respectively, the weight being greater than a weight associated with other scan data.

5. The X-ray CT apparatus according to claim 1, wherein the data processing device further performs:
a step of associating a weight with scan data further adjacent to the scan data adjacent to the anomalous scan data, the weight being smaller than a weight associated with scan data adjacent to the anomalous scan data but greater than a weight associated with the other scan data.

6. The X-ray CT apparatus according to claim 1, wherein the data processing device performs:
a step of gradually decreasing a weight to be associated with scan data adjacent to the anomalous scan data, every time the iterative operation is iterated, so as to eventually equal to a weight associated with the other scan data.

7. The X-ray CT apparatus according to claim 1, wherein the data processing device further performs:
a step of associating a weight with the anomalous scan data, the weight being greater than or equal to "0" but smaller than or equal to a weight associated with the other scan data.

8. A method for generating an X-ray CT image, for use in an X-ray CT apparatus including:
an X-ray generator that generates X-rays;
an X-ray detector that is configured to have multiple X-ray detecting elements arranged in array for detecting intensity of the X-rays;
a scanning control unit that transmits detection data detected by the X-ray detecting elements as scan data of a subject; and
a data processing device that obtains the scan data transmitted from the scanning control unit, and processes the obtained scan data to generate an X-ray CT image of the subject,
the method comprising steps, performed by the data processing device, of:
storing the scan data obtained by the X-ray detecting elements into a storage unit in accordance with an arrangement of the X-ray detection elements in the X-ray detector, and detecting anomalous scan data among the stored scan data;
associating a weight with scan data adjacent to the anomalous scan data detected, the weight being greater than a weight associated with other scan data; and
calculating pixel data of the X-ray CT image of the subject, through iteration of an iterative operation using a projection matrix defined by data including a layout position of the X-ray generator and arrangement positions of the respective multiple X-ray detection elements, pixel data that has been set at that time, and the scan data,
wherein in the iterative operation, when calculating an update amount for the pixel data based on difference data between projection data obtained from the projection matrix and the pixel data at that time, and the scan data, the difference data is weighted with the weight associated with the scan data corresponding to the difference data.

9. The method for generating an X-ray CT image according to claim 8, wherein if the anomalous scan data is caused by a failure of an X-ray detecting element of multiple X-ray detecting elements that constitute the X-ray detector,
the method comprises a step, performed by the data processing device, of:
associating a weight with scan data obtained from X-ray detecting elements adjacent to the fault X-ray detecting element, the weight being greater than a weight associated with other scan data.

10. The method for generating an X-ray CT image according to claim 9, wherein the method comprises a step of:
when associating a weight with the scan data obtained from the X-ray detecting elements adjacent to the fault X-ray detecting element, associating a weight, which is greater than a weight associated with the other scan data, with scan data obtained from the X-ray detecting elements adjacent in the channel direction to the fault X-ray detecting element.

11. The method for generating an X-ray CT image according to claim 8, wherein if the anomalous scan data is caused by an anomalous fluctuation of X-rays generated by the X-ray generator,
the method comprises a step of:
associating a weight with scan data obtained at a time one unit of time before and after the time when the anomalous fluctuation of X-rays has been detected, respectively, the weight being greater than a weight associated with other scan data.

12. The method for generating an X-ray CT image according to claim 8, wherein the method further comprises a step of:
associating a weight with scan data further adjacent to the scan data adjacent to the anomalous scan data, the weight being smaller than a weight associated with scan data adjacent to the anomalous scan data but greater than a weight associated with the other scan data.

13. The method for generating an X-ray CT image according to claim 8, wherein the method comprises a step of:
gradually decreasing a weight to be associated with scan data adjacent to the anomalous scan data, every time the iterative operation is iterated, so as to eventually equal to a weight associated with the other scan data.

14. The method for generating an X-ray CT image according to claim 8, wherein the method further comprises a step of:
associating a weight with the anomalous scan data, the weight being greater than or equal to "0" but smaller than or equal to a weight associated with the other scan data.

* * * * *